United States Patent
Rovatti et al.

(10) Patent No.: US 9,931,456 B2
(45) Date of Patent: Apr. 3, 2018

(54) APPARATUS AND METHOD TO CHECK EXTRACORPOREAL CIRCUIT

(71) Applicant: GAMBRO LUNDIA AB, Lund (SE)

(72) Inventors: Paolo Rovatti, Finale Emilia (IT); Fabio Roncadi, Reggio Emilia (IT); Bruno Genovese, Rome (IT); Pier Giorgio Verdi, Bologna (IT)

(73) Assignee: Gambro Lundia AB, Lund (SE)

( * ) Notice: Subject to any disclaimer, the term of this patent is extended or adjusted under 35 U.S.C. 154(b) by 226 days.

(21) Appl. No.: 14/369,805

(22) PCT Filed: Dec. 21, 2012

(86) PCT No.: PCT/IB2012/057632
§ 371 (c)(1),
(2) Date: Jun. 30, 2014

(87) PCT Pub. No.: WO2013/098750
PCT Pub. Date: Jul. 4, 2013

(65) Prior Publication Data
US 2015/0135804 A1    May 21, 2015

Related U.S. Application Data

(60) Provisional application No. 61/581,148, filed on Dec. 29, 2011.

(30) Foreign Application Priority Data

Dec. 29, 2011  (EP) .................................... 11010268

(51) Int. Cl.
*A61M 1/36* (2006.01)
*G01M 3/28* (2006.01)

(52) U.S. Cl.
CPC ........ *A61M 1/3639* (2013.01); *A61M 1/3643* (2013.01); *A61M 1/3644* (2014.02);
(Continued)

(58) Field of Classification Search
CPC ......................... A61M 1/3643; G01M 3/2846
(Continued)

(56) References Cited

U.S. PATENT DOCUMENTS 5,810,758 A * 9/1998 Yamazaki ............... A61M 1/10
                                                          604/6.09
2008/0214981 A1 * 9/2008 Delnevo ............. A61M 1/3643
                                                          604/6.16
(Continued)

FOREIGN PATENT DOCUMENTS

WO    2006123197    11/2006
WO    2008/125894   10/2008
(Continued)

OTHER PUBLICATIONS

International Search Report cited in PCT/IB2012/057632 dated May 29, 2013.

*Primary Examiner* — Walter L Lindsay, Jr.
*Assistant Examiner* — Philip Marcus T Fadul
(74) *Attorney, Agent, or Firm* — K&L Gates LLP

(57) ABSTRACT

An extracorporeal treatment assembly including a pump and a controller wherein an extracorporeal circuit is mounted to the assembly, the controller causes the assembly to: control the pump to pump liquid through the passage and the flow coupling; collect actual fluid pressure data; store circuit type data uniquely corresponding to a certain type of extracorporeal circuit; determine a dimension of the certain type of extracorporeal circuit; determine an expected fluid pressure for the certain type of extracorporeal circuit; based on a comparison of the actual fluid pressure data and the expected
(Continued)

fluid pressure, determine whether the certain type of extracorporeal circuit corresponds to the actual extracorporeal circuit.

34 Claims, 6 Drawing Sheets

(52) U.S. Cl.
CPC ...... *G01M 3/2846* (2013.01); *A61M 2205/18* (2013.01); *A61M 2205/3355* (2013.01); *A61M 2205/50* (2013.01); *A61M 2205/70* (2013.01)

(58) Field of Classification Search
USPC ............................................................ 73/40
See application file for complete search history.

(56) References Cited

U.S. PATENT DOCUMENTS

2010/0114005 A1* 5/2010 Rovatti .................. A61M 1/16
 604/6.15
2013/0177455 A1* 7/2013 Kamen ............... G06F 19/3418
 417/313

FOREIGN PATENT DOCUMENTS

| WO | 2009051669 | 4/2009 |
| WO | 2009094183 | 7/2009 |

* cited by examiner

APPARATUS AND METHOD TO CHECK EXTRACORPOREAL CIRCUIT

This application is the U.S. national phase of International Application No. PCT/IB2012/057632 filed 21 Dec. 2012 which designated the U.S. and claims priority to EP 11010268.8 filed 29 Dec. 2011, and U.S. Provisional Patent Application Ser. No. 61/581,148 filed 29 Dec. 2011, the entire contents of each of which are hereby incorporated by reference.

BACKGROUND OF THE INVENTION

The invention relates to extracorporeal treatment systems and methods, and particularly to verifying the connection of an extracorporeal circuit to an extracorporeal treatment assembly.

Extracorporeal treatment assemblies typically treat blood withdrawn from a patient and infuse the treated blood into the patient. These assemblies generally include an extracorporeal treatment apparatus having a pump or pumps, a blood treatment device and a separable extracorporeal circuit having blood and other liquid passages. The extracorporeal treatment apparatus may be a monitor for hemodialysis and hemo(dia)filtration and the treatment device may be a blood filter. The separable extracorporeal circuit may be a blood tubing set which attaches to the monitor.

Prior to a blood treatment session, an extracorporeal circuit is selected, mounted to the extracorporeal treatment apparatus and primed with a liquid. Priming generally involves flushing the passages in the extracorporeal circuit with priming liquid to purge gases from the passages. The blood treatment session commences after the circuit has been filled with the priming liquid and the gases flushed from the passages in the circuit. During the blood treatment session, the blood passages in the circuit may receive blood withdrawn from a patient, move the blood through a blood treatment device and infuse the treated blood into the patient. After the blood treatment session, the circuit may be removed from the apparatus and disposed of such as by being treated as medical waste.

An extracorporeal treatment apparatus may operate with various types of extracorporeal circuits. For example, an extracorporeal treatment apparatus may be configured to receive an extracorporeal circuit for normal sized adult patients, an extracorporeal circuit for pediatric patients, and a Low Weight Low Volume (LWLV) blood circuit for smaller adults. To start a blood treatment session, a human operator selects the type of extracorporeal circuit corresponding to the patient. The operator mounts the selected circuit to the apparatus. The operator may also enter operational settings for a desired treatment mode and information regarding the patient, e.g., normal sized adult, child or small adult, into the controller for the treatment apparatus.

The different types of extracorporeal circuits may differ in the sizes of their liquid flow passages circuit. The blood passages for the LWLV and pediatric circuits may have smaller diameters than the blood passages in a circuit for the normal sized adult. The difference in sizes of the passages affects the amount of liquid moved through the passage during each pump rotation.

The operational settings of the treatment apparatus cause the pump to rotate at rates intended to cause a certain rate of liquid to flow through the passages in the circuit. The operational settings for the extracorporeal treatment system may differ for each of the different types of circuits. For example, the pump speed may be faster for a normal sized circuit than for the LWLV circuit or the pediatric circuit.

If the wrong circuit is connected to the treatment apparatus, the operational settings may cause the pumps to withdraw or infuse blood and other liquids at rates different than the prescribed rates for the treatment. In particular, the rate of blood withdrawal or infusion may differ from the desired rates if the wrong type of blood circuit is connected to the treatment apparatus.

In view of the potential for the withdrawal or infusion of liquids at non-prescribed rates, there is a long felt need for an automatic process to detect whether the extracorporeal circuit connected to an extracorporeal treatment apparatus is the type of circuit that corresponds to the operational settings of the apparatus. Further, there is a long felt need for an automatic process to confirm or determine that an appropriate extracorporeal circuit is connected to an extracorporeal treatment apparatus.

BRIEF DESCRIPTION OF THE INVENTION

An extracorporeal apparatus and method has been conceived and is disclosed here to automatically: (i) identify the extracorporeal circuit mounted to the extracorporeal treatment apparatus and match the identified circuit to the operational settings for the apparatus, and (ii) determine whether a passage or passages is leaking in the circuit. During a startup procedure, such as a priming procedure, a controller for the extracorporeal treatment apparatus performs a pressure check on an extracorporeal circuit mounted to the apparatus. The pressure check is used to determine if the proper circuit is connected to the apparatus and if there is a leak in the circuit.

An extracorporeal treatment apparatus has been conceived and invented which is configured to receive an removable extracorporeal circuit, the treatment apparatus includes: a pump configured to pump a liquid through a passage in the extracorporeal circuit; a flow coupling connectable to an outlet end of the passage, wherein the impedance to liquid flow through the passage at the flow coupling is a constant or known value; a controller including a processor and an electronic memory storing instructions, data regarding operational settings of the treatment apparatus and data correlating different types of the extracorporeal circuits to specific operational settings, the instructions when executed by the processor cause the controller to: (i) actuate the pump to move the liquid through the passage while the outlet of the passage is connected to the flow coupling; (ii) receive data indicative of a pressure of the liquid flowing through the passage from a pressure sensor monitoring the pressure of the liquid; (iii) identify if a pressure range in the stored data corresponds to the received data indicative of the pressure in the passage; (iv) correlate the identified pressure range to a particular type of extracorporeal circuit, and (v) determine if the identified circuit type corresponds to the operational settings of the treatment apparatus or identify the operational settings for the treatment apparatus that conform to the identified circuit type.

The received pressure data may be data output by a pressure sensor monitoring the pressure of a priming liquid flowing through the passage. The instructions may be executed by the controller during a priming operation of the apparatus. The data indicative of the pressure may be received during a portion of the priming process occurring after the priming fluid has filled the passages in the circuit.

The instructions, when executed by the processor, may also cause the controller to automatically confirm that the outlet to the passage is connected to flow coupling prior to the actuation of the pump. This confirmation may include a determination that a door covering a connection to the drainage container is open to indicate that the outlet of the liquid passage is connected to the drainage container.

The flow coupling may be a coupling to the drainage container included in the treatment apparatus. The flow impedance at the flow coupling may be due to a flow restriction having a smaller cross-sectional flow area than does any other portion of the liquid passage extending from the pump to the outlet. The flow restriction may be a connector included in an inlet portion of the drainage container, such as a Luer connector.

A method has been conceived and invented to monitor a liquid flow through a passage in an extracorporeal circuit connected to an extracorporeal treatment apparatus having a pump, the method comprising: connecting the passage to the pump; connecting the outlet of the passage to a container having a known or constant flow impedance; pumping liquid through the passage and into the container; sensing a value of a condition of the pump while pumping the liquid or of the liquid flowing through the passage between the pump and the container; and determining whether the sensed value differs from an expected value for the condition.

An extracorporeal treatment assembly has been conceived and invented comprising: an extracorporeal treatment apparatus including a pump configured to move a liquid through a liquid passage mountable to the pump and a controller that governs the pump; an extracorporeal circuit connectable to the treatment apparatus, wherein the circuit includes the liquid passage mountable to the pump; a drainage container connectable to the liquid passage, wherein the drainage connector includes a connector configured to connect to the liquid passage, wherein the connector has a known impedance to the flow of liquid from the liquid passage into the drainage container; a pressure sensor configured to sense a liquid pressure in the passage; a memory storing a correlation between an expected pressure value for at least one type of a plurality of types of the extracorporeal circuit, and the controller which: (i) governs the pump to move liquid drawn into the extracorporeal circuit from the source of the liquid and pump the liquid through the liquid passage and into the drainage container; (ii) monitors pressure data from the pressure sensor while the liquid flows through the liquid passage, (iii) generates an alarm if the pressure data indicates the pressure of the liquid in the liquid passage does not conform to the expected pressure value.

The extracorporeal treatment assembly may include a blood treatment device having a blood chamber and a liquid chamber separated by porous membrane from the blood chamber, and the inlet to the extracorporeal circuit and the liquid passage are in fluid communication with the blood chamber. The liquid may be a primping liquid and the source is a source of the priming liquid.

In accordance with a first main independent aspect an extracorporeal treatment apparatus configured to receive an extracorporeal circuit has been provided, the treatment apparatus comprising a pump configured to pump a liquid through a passage in the extracorporeal circuit while the circuit is mounted to the treatment apparatus; a flow coupling connectable to an outlet of the passage, the flow impedance at the flow coupling is a constant or known value; and a controller which is configured to: control the pump to move liquid through the passage, and the flow coupling; collect data indicative of a pressure condition of the liquid flowing through the passage and flow coupling; identify a parameter value which correlates to the indicated pressure condition, wherein the identified parameter value is one a plurality of known parameter values or ranges, wherein each value or range of values uniquely corresponds to a circuit type of a plurality extracorporeal circuit types that may be mounted to the treatment apparatus, and determine an operational setting for the treatment apparatus or determine whether a current operational setting is proper based on the type of extracorporeal circuit corresponding to the identified parameter value.

In accordance with a first auxiliary independent aspect an extracorporeal treatment apparatus configured to receive an extracorporeal circuit has been provided, the treatment apparatus comprising a pump configured to pump a liquid through a passage in the extracorporeal circuit while the circuit is mounted to the treatment apparatus; a flow coupling connectable to an outlet of the passage, the flow impedance at the flow coupling is a constant or known value; and a controller which is configured to: store a flow resistance value at the flow coupling, said flow resistance value being either a value set by the operator before starting apparatus or a pre-stored constant value known by the controller before starting the apparatus; control the pump at a speed corresponding to a set fluid flow value to move liquid through the passage, and the flow coupling; collect actual data indicative of a pressure condition of the liquid flowing through the passage and flow coupling during control of the pump at said speed; store a data uniquely corresponding to an expected circuit type mounted to the treatment apparatus out of a plurality extracorporeal circuit types that may be mounted to the treatment apparatus, optionally said data being acquired by the apparatus or set by the operator before starting the operation of the apparatus; retrieving a sectional dimension of the mounted circuit type based on said data uniquely corresponding to the mounted circuit type; determine the expected data indicative of an expected pressure value of the liquid flowing through the passage and flow coupling as a function of the set fluid flow value or pump speed and of the sectional dimension of the mounted circuit type and as a function of said flow resistance value; comparing the expected data with the actual data; determining as a function of the comparing step whether the expected circuit type corresponds to the circuit type actually mounted on the apparatus.

In accordance with a second aspect depending on any of the 1st aspects the received data is data output by a pressure sensor monitoring the pressure of the liquid flowing through the passage.

In accordance with a 3rd aspect depending on the previous aspects the extracorporeal treatment apparatus further comprises a pressure sensor monitoring the pressure of the liquid flowing through the passage, a signal from the pressure sensor being received by the controller.

In accordance with a 4th aspect depending on the previous aspects the data indicative of the pressure is collected during a priming operation of the apparatus.

In accordance with a 5th aspect depending on the previous aspects the controller is configured to perform the steps of controlling, collecting, identifying and determining during a priming operation of the apparatus and/or before starting an extracorporeal blood treatment operation, in particular at least the steps of controlling and collecting being performed during a priming operation of the apparatus and the steps of identifying and/or determining being performed either during a priming operation of the apparatus or after the priming operation and before starting the extracorporeal blood treatment operation In accordance with a 6th aspect depending on the previous aspects 4 or 5 the data indicative of the pressure is received substantially at the end of the priming.

In accordance with a 7th aspect depending on the previous aspects the flow coupling includes an inlet coupling to a liquid drain, such as a liquid container included in the treatment apparatus.

In accordance with a 8th aspect depending on the previous aspects the flow impedance at the flow coupling is due to a flow restriction having a smaller cross-sectional flow area for the liquid than does any portion of the liquid passage extending from the pump to the flow coupling.

In accordance with a 9th aspect depending on the previous aspects the flow coupling includes a protruding portion configured to connect to outlet of the passage by direct insertion into outlet of the passage, the protruding portion defining internally a flow conduit receiving the fluid and directing the fluid towards a liquid drain.

In accordance with a 10th aspect depending on the previous aspect the protruding portion is in the form of a substantially circular tube, said tube having in particular a smooth outer lateral surface without means for attaching to the passage.

In accordance with a 11th aspect depending on the previous aspects 9 or 10 the flow coupling includes an external crown at least partially embracing the protruding portion, the external crown including a structure for attaching to the passage.

In accordance with a 12th aspect depending on the previous aspects the flow coupling comprises a male Luer connector for coupling to a corresponding female Luer connector of the passage.

In accordance with a 13th aspect depending on the previous aspects the controller is configured to further automatically check that the passage is connected to the flow coupling prior to the actuation of the pump.

In accordance with a 14th aspect depending on the previous aspects the apparatus comprises a sensor configured to sense a specific condition of the flow coupling, said specific condition being either a non coupled condition of the flow coupling to the passage or a condition in which coupling between the flow coupling and the passage is possible.

In accordance with a 15th aspect depending on the previous aspect the specific condition sensed by the sensor is a condition of open door allowing coupling of the flow coupling to the passage or of closed door indicating a non coupled condition of the flow coupling to the passage.

In accordance with a 16th aspect depending on the previous aspects the confirmation that the liquid passage is connected to the drainage container includes determining if a door covering a liquid connection is open.

In accordance with a 17th aspect depending on the previous aspects the flow coupling includes a connector included in an inlet portion of a drainage container.

In accordance with a 18th aspect depending on the previous aspects the flow coupling includes a Luer connector.

In accordance with a 19th aspect depending on the previous aspects the controller is configured to sense the liquid pressure for a certain period of pumping, and the sensed pressure determined based on several pressure sensing events during the certain period.

In accordance with a 20th aspect depending on the previous aspect the sensed pressure is an average of the pressures measured during the pressure sensing events.

In accordance with a 21st aspect depending on the previous aspects the extracorporeal circuit may be one of a plurality of selectable types of circuits and the liquid passage in at least one of the circuit types has a different size than the liquid passage in another one of the circuit types.

In accordance with a 22nd aspect depending on the previous aspects the pump is an occlusive pump, particularly a peristaltic pump, and the passage is a deformable tube, wherein the pumping includes the pump pinching the tube to move the priming liquid through the passage.

In accordance with a 23rd aspect depending on the previous aspects the flow impedance at the flow coupling is the flow resistance at the flow coupling.

In accordance with a 24th aspect depending on the previous aspects the controller has a memory storing a flow resistance value at the flow coupling, said flow resistance value being either a value set by the operator before starting apparatus or a pre-stored constant value known by the controller before starting the apparatus.

In accordance with a 25th aspect depending on the previous aspects the controller is not configured to calculate a flow resistance of the flow coupling.

In accordance with a 26th aspect depending on the previous aspects the flow coupling determines a local loss of head in the extracorporeal circuit.

In accordance with a 27th aspect depending on the previous aspects the controller is configured to: control the pump at a speed corresponding to a set fluid flow value to move liquid through the passage, and the flow coupling; collect actual data indicative of a pressure condition of the liquid flowing through the passage and flow coupling during control of the pump at said speed; store a data uniquely corresponding to an expected circuit type mounted to the treatment apparatus out of a plurality extracorporeal circuit types that may be mounted to the treatment apparatus, optionally said data being acquired by the apparatus or set by the operator before starting the operation of the apparatus; retrieving a sectional dimension of the mounted circuit type based on said data uniquely corresponding to the mounted circuit type; determine an expected data indicative of an expected pressure value of the liquid flowing through the passage and flow coupling as a function of the set fluid flow value or pump speed and of the sectional dimension of the mounted circuit type; comparing the expected data with the actual data; determining as a function of the comparing step whether the expected circuit type corresponds to the circuit type actually mounted on the apparatus.

In accordance with a 28th aspect depending on the previous aspect the controller is further configured to store a flow resistance value at the flow coupling, said flow resistance value being either a value set by the operator before starting apparatus or a pre-stored constant value known by the controller before starting the apparatus; determine the expected data indicative of an expected pressure value of the liquid flowing through the passage and flow coupling as a function of the set fluid flow value or pump speed and of the sectional dimension of the mounted circuit type and as a function of said flow resistance value.

In accordance with a 29th aspect depending on the previous aspects the controller is further configured to determine an operational setting for the treatment apparatus or determine whether a current operational setting is proper based on the type of extracorporeal circuit corresponding to the identified parameter value.

In accordance to a 30th independent aspect an extracorporeal treatment system is provided comprising an extracorporeal treatment apparatus in accordance with anyone of the previous aspects and an extracorporeal circuit, the extracorporeal circuit including at least a passage having an outlet connectable to the flow coupling.

In accordance with a 31st aspect depending on the previous aspect the flow coupling has a flow restriction with a cross-sectional flow area smaller than a cross-sectional flow area of the passage.

In accordance with a 32nd aspect depending on the previous aspects 30 or 31 the flow coupling has a flow restriction with a cross-sectional flow area smaller than a cross-sectional flow area of any portion of the passage extending from the pump to the flow coupling.

In accordance with a 33rd aspect depending on the previous aspects 30 to 32 the extracorporeal circuit is mounted on the apparatus with the pump configured to act on the passage and the outlet of the passage connected to the flow coupling.

In accordance with a 34th aspect depending on the previous aspects 30 to 33 the outlet of the passage has a cross-sectional flow area configured to receive a protruding portion of the flow coupling to connect by insertion into outlet of the passage, the protruding portion defining internally a flow conduit receiving the fluid and directing the fluid towards a liquid drain.

In accordance with a 35th aspect depending on the previous aspects 30 to 34 the flow coupling protruding portion coupled to the passage determines a local loss of head in the extracorporeal circuit.

In accordance with a 36th aspect depending on the previous aspects 30 to 35 the extracorporeal circuit comprises at least a treatment unit having at least a first chamber and at least a second chamber separated from one another by a semipermeable membrane; at least a blood removal line connected to an inlet port of the first chamber and configured to remove blood from a patient, at least a blood return line connected with an outlet port of the first chamber and configured to return treated blood to the patient, the blood removal line, said passage being defined by a portion of the blood removal line or by a portion of the blood return line.

In a further independent 37th aspect a method to monitor a continuous liquid flow through a liquid passage in an extracorporeal circuit connected to an extracorporeal treatment apparatus having a pump is provided, the method comprising connecting the liquid passage to the pump;

connecting the outlet of the liquid passage to a device having a known or constant flow impedance; pumping liquid through the liquid passage and into or through the device; sensing a value of a condition of the pump while pumping the liquid or of the liquid flowing through the passage between the pump and the device, and issuing a notice or ceasing pumping if the sensed value differs from an expected value for the condition.

In accordance with a 38th aspect depending on the previous aspect the sensed value and the condition is a pressure of the liquid flowing through the passage.

In accordance with a 39th aspect depending on the previous aspects 37 or 38 the sensed value is electrical current amperes and the condition is electrical current driving the pump.

In accordance with a 40th aspect depending on the previous aspects 37 to 39 the liquid is a priming liquid and the pumping occurs while priming the circuit.

In accordance with a 41st aspect depending on the previous aspect the sensing of the liquid pressure occurs during an end portion of the priming.

In accordance with a 42nd aspect depending on the previous aspects 37 to 41 the sensing of the liquid pressure occurs while the liquid flows through the flow restriction.

In accordance with a 43rd aspect depending on the previous aspect the flow restriction has a smaller cross-sectional flow area for the liquid than does any portion of the liquid passage extending from the pump to the outlet.

In accordance with a 44th aspect depending on the previous aspects 37 to 43, the method further comprises automatically confirming that an outlet to the liquid passage is connected to the drainage container prior to the pumping step.

In accordance with a 45th aspect depending on the previous aspect the confirmation that an outlet of the liquid passage is connected to the drainage container includes determining if a door covering a liquid connection to the drainage device is open which indicates that the outlet of the liquid passage is connected to the drainage container.

In accordance with a 46th aspect depending on the previous aspects 37 to 45 the flow restriction is in a connector included in an inlet portion of the drainage container.

In accordance with a 47th aspect depending on the previous aspects 37 to 46 the flow restriction is in a Luer connector included as part of the drainage container.

In accordance with a 48th aspect depending on the previous aspects 37 to 47 the liquid pressure is sensed for a certain period of pumping, and the sensed pressure determined based on several pressure sensing events during the certain period.

In accordance with a 49th aspect depending on the previous aspect the sensed pressure is an average of the pressures measured during the pressure sensing events.

In accordance with a 50th aspect depending on the previous aspects 37 to 49 the extracorporeal circuit may be one of a plurality of selectable types of circuits and the liquid passage in at least one of the circuit types has a different size than the liquid passage in another one of the circuit types, wherein the sensed liquid pressure will depend on the circuit type connected to the extracorporeal apparatus.

In accordance with a 51st aspect depending on the previous aspects 37 to 50 the method further comprises the following steps: control the pump at a speed corresponding to a set fluid flow value to move liquid through the passage, and the flow coupling; collect actual data indicative of a pressure condition of the liquid flowing through the passage and flow coupling during control of the pump at said speed; store a data uniquely corresponding to an expected circuit type mounted to the treatment apparatus out of a plurality extracorporeal circuit types that may be mounted to the treatment apparatus, optionally said data being acquired by the apparatus or set by the operator before starting the operation of the apparatus; retrieving a sectional dimension of the mounted circuit type based on said data uniquely corresponding to the mounted circuit type; determine an expected data indicative of an expected pressure value of the liquid flowing through the passage and flow coupling as a function of the set fluid flow value or pump speed and of the sectional dimension of the mounted circuit type; comparing the expected data with the actual data; determining as a function of the comparing step whether the expected circuit type corresponds to the circuit type actually mounted on the apparatus.

In accordance with a 52nd aspect depending on the previous aspect the method further comprises the following step: determine an operational setting for the treatment apparatus or determine whether a current operational setting is proper based on the type of extracorporeal circuit corresponding to the identified parameter value.

In accordance with a 53rd aspect depending on the previous aspect the method further comprises the following steps: store a flow resistance value at the flow coupling, said flow resistance value being either a value set by the operator before starting apparatus or a pre-stored constant value known by the controller before starting the apparatus; determine the expected data indicative of an expected pressure value of the liquid flowing through the passage and flow coupling as a function of the set fluid flow value or pump speed and of the sectional dimension of the mounted circuit type and as a function of said flow resistance value.

In accordance with a 54th aspect depending on the previous aspects 37 to 53 the method further comprises the step of recalling from a memory a flow resistance of the flow coupling without previously calculating it.

In accordance with a 55th aspect depending on the previous aspects 37 to 54 the method further comprises the step of: storing a flow resistance value at the flow coupling, said flow resistance value being either a value set by the operator before starting apparatus or a pre-stored constant value known by the controller before starting the apparatus.

In accordance with a 56th aspect depending on the previous aspects 37 to 55 the flow impedance at the flow coupling is the flow resistance at the flow coupling.

It is also known from document WO2008/125894 an apparatus for extracorporeal blood treatment having an extracorporeal circuit connected to a blood chamber of a membrane device. A pump displaces a priming fluid from a source of a priming fluid to a drainage for discharging the priming fluid. A control unit is provided with a processor which controls the pump at a preset first flow rate value, and receives from a pressure sensor a first pressure value, compares the first pressure value with a reference pressure value and, on the basis of this comparison, determines whether or not the extracorporeal circuit is of a pediatric type or of an adult type.

BRIEF DESCRIPTION OF THE DRAWINGS

FIGS. 5 and 6 are perspective views of an exemplary priming liquid discharge container, wherein FIG. 5 shows the cover doors opened and FIG. 6 shows the doors closed.

DETAILED DESCRIPTION OF THE INVENTION

Figure 1:
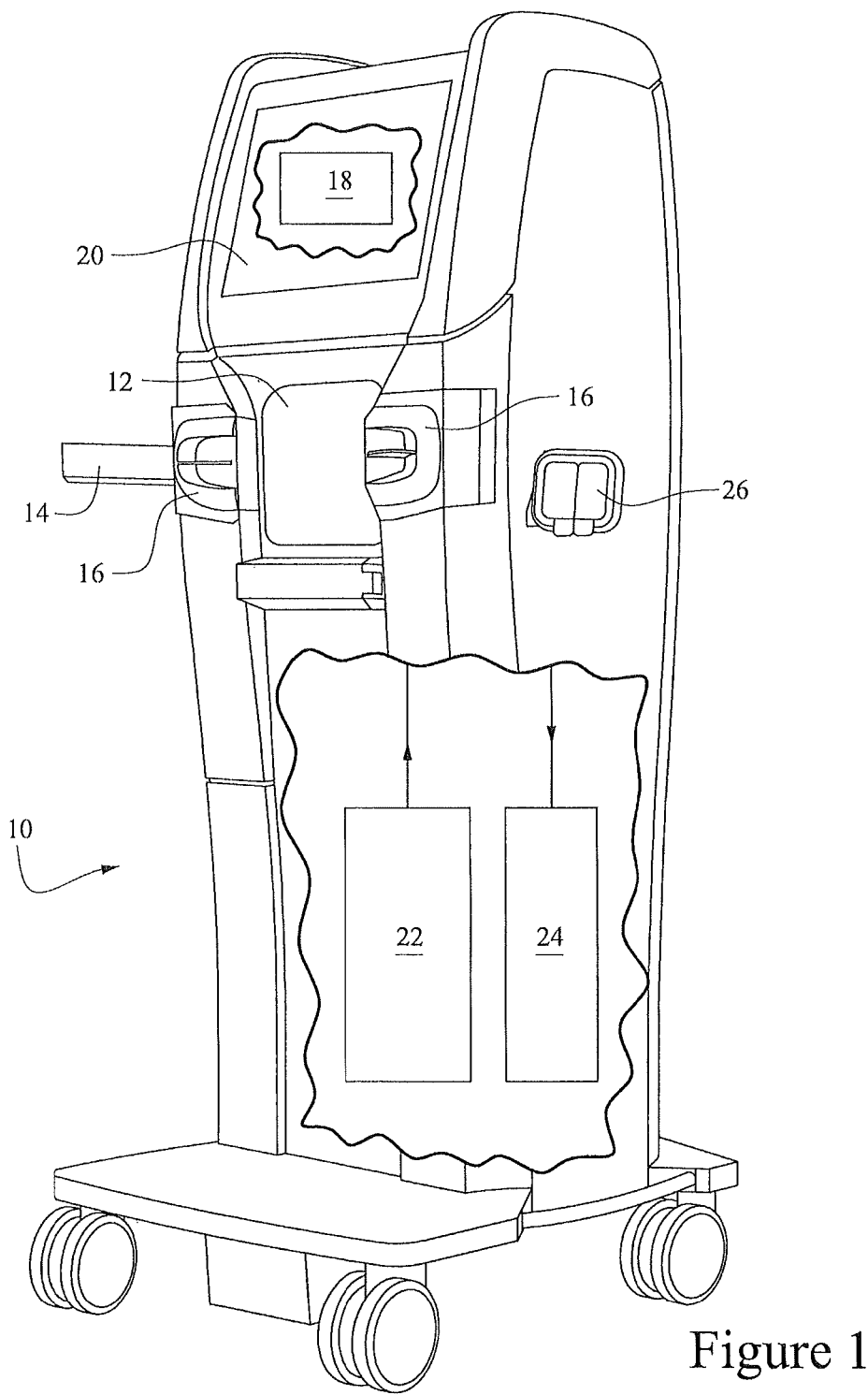
FIG. 1 is a perspective view of an extracorporeal treatment apparatus in which portions of the housing have been cut away to show an internal liquid container and a drainage container.

FIG. 1 is a schematic diagram of an extracorporeal treatment assembly 10 which is adapted to receive a separable blood circuit. The treatment assembly may be a monitor for hemodialysis, hemo(dia)filtration, ultrafiltration, treatment and infusion of blood or other extracorporeal treatment of a mammalian patient, such as a human. The treatment assembly includes a mount 12 to receive an extracorporeal circuit, and a mount 14 to receive a blood treatment device, such as a blood filter.

The treatment assembly 10 houses one or more pumps 16, e.g., peristaltic pump or other positive displacement pump that moves blood and other liquids through tubular passages in the extracorporeal circuit. The pumps 16 are graphically represented by a recessed U-shaped track for rotating pump rollers. The tubular passages are placed in the track and pinched by the rollers of the pump. As the rollers turn, they force liquids through the passages at a rate corresponding to the rotational speed of the pump.

The pumps, e.g., the motors turning the rollers, may be controlled by a controller, e.g., controller 18, housed within the assembly 10. The controller may include a computer processor(s) and electronic storage for data and program instructions. The stored data may include operational settings for various treatments to be performed with the extracorporeal treatment apparatus, sensor measurements including measurements of liquids flowing in the tubes, and inputs manually made by an operator of the apparatus. The stored operational settings may be pump speeds, treatment duration and ranges of expected pressures of liquids in the passages during the various treatments that can be performed by the apparatus. Associated with each of the treatments may be a type of extracorporeal circuit, wherein the operational settings for a treatment are based on the prescribed type of extracorporeal circuit being mounted to the apparatus 10.

The controller 18 may control a graphical user input and display system 20 which may be a touch screen display. The controller may generate for the input and display system 20 text, data or other graphical representations of the operational settings of the assembly and information regarding current operational conditions, such as pressures in the passages of the circuit. The input and display system 20 may include input devices, such as keys, knobs and graphical icons, to be used by a human operator to input settings to the apparatus. For example, the operator may input settings specifying a selected treatment and type of patient to receive the treatment. The controller receives the input data and uses the data to select a corresponding control setting stored in the memory of the controller.

The controller may include an electronic memory storing data correlating the expected pressure in the liquid passage during the pressure check for treatment mode of the extracorporeal treatment apparatus. The controller compares the pressure data obtained during the pressure check to the expected pressure range corresponding to the type of extracorporeal circuit that should be connected to the treatment apparatus. If the sensed pressure level is outside the expected range, the controller issues an alarm to alert the user that an improper extracorporeal circuit has been mounted to the apparatus. The controller may not allow blood treatment to start if the sensed pressure level is outside of the expected range in addition to or as an alternative to issuing an alarm.

In addition to governing the pumps 16 connected to the circuit, the controller 18 may also control other pumps, valves, heating devices and other systems housed in the apparatus to generate priming liquids and treatment solutions to be used with the extracorporeal circuit and treatment session. The apparatus may store liquids 22 for priming and generation of treatment solutions.

In addition, the apparatus may have a drainage for example a drainage container 24 for receiving used priming liquid, filtrate liquids and used treatment solutions. The drainage, for example the drainage container, may have an inlet coupling 26 attached to the housing for the apparatus. The inlet coupling may be, for example, part of a Luer connector, which is adapted to couple to a matching Luer connector on the end of a liquid passage of the extracorporeal circuit.

Figure 2:
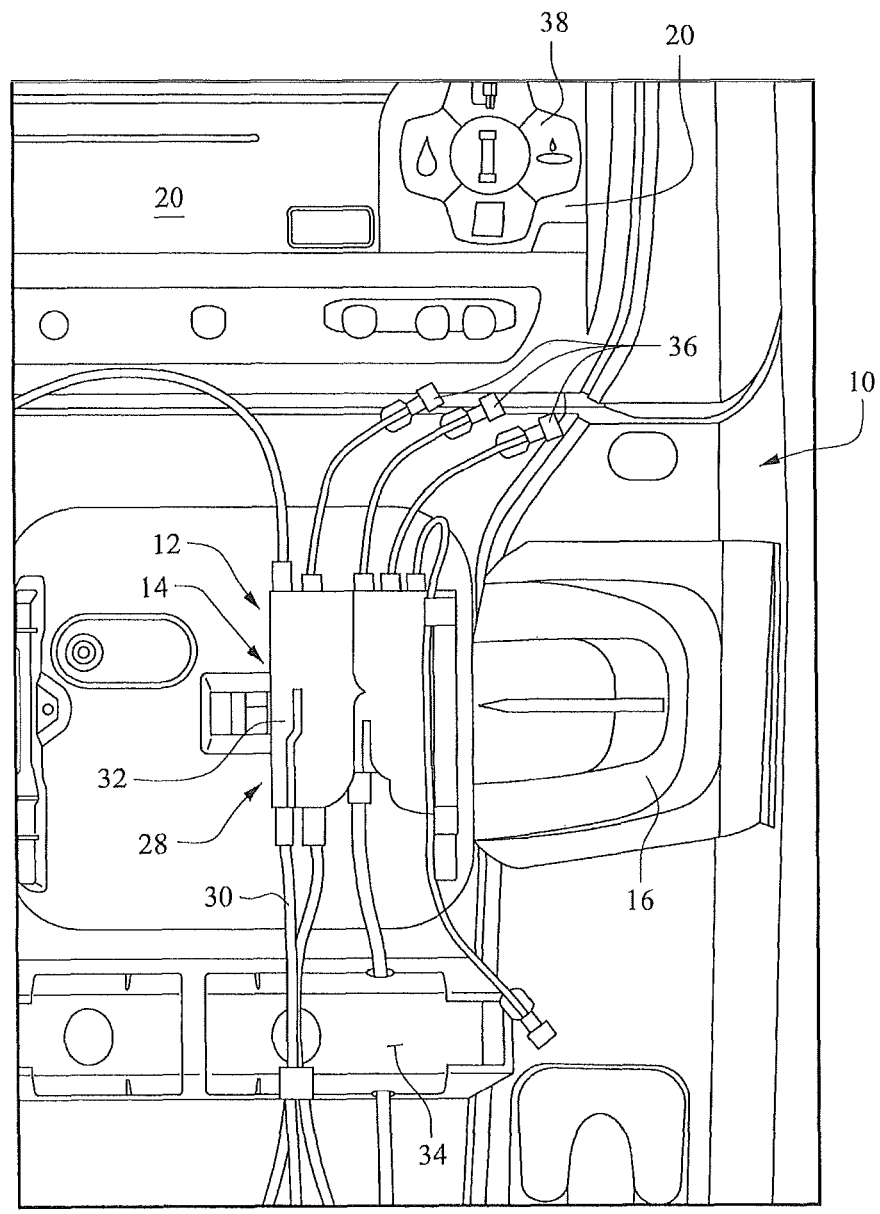
FIG. 2 is a front view of the extracorporeal circuit mounted to the extracorporeal treatment apparatus.

FIG. 2 is a front view of a portion of the extracorporeal treatment apparatus 10 on which is mounted an extracorporeal circuit 28. The circuit 28 may comprise flexible hollow plastic tubular passages (or tubes) 30 and a rigid plastic frame (or cassette) 32 that supports the passages.

The frame 32 attaches to the mount 14 on the apparatus 10. The back of the frame 32 may include a fastener which connects to a matching fastener of the mount 14.

Mounting the frame 32 to the treatment apparatus aligns the tubes 30 with the pumps 16, sensors (indicated by sensor cover 34) and other components of the treatment apparatus. The sensors may include one or more pressure sensors which measures the pressure in the tubes.

The ends of the tubes may include a connector 36, such as a Luer connector which may be a slip or locking connector.

In general the extracorporeal circuit 28 may include an arterial line including a main tract having one end configured to be connected to a patient for withdrawing blood and the other end connected to a first (or arterial) chamber of the rigid frame 32. A second tract of the arterial line receives blood from the arterial chamber and allows directing it towards the treatment unit (e.g. dialyzer).

A venous line receives the treated blood form the treatment unit and a main tract of the venous line brings the blood to a second (venous chamber) of the rigid frame 32. A second tract of the venous line has one end connected to the venous chamber and the other end connectable to a patient to return the treated blood.

Either one or both the arterial and venous chambers includes a pressure sensor to detect the respective blood pressure. In particular the pressure sensor/s is/are placed on an upper portion of the camber destined to be occupied by air during treatment/priming procedures.

The extracorporeal apparatus 10 may receive different types of extracorporeal circuits. The types of extracorporeal circuits may include a circuit for normal sized adult patients, a circuit for pediatric patients which has relatively small diameter tubes, and a Low Weight Low Volume (LWLV) circuit for smaller adults which may also having small diameter tubes. The appropriate circuit to be mounted to the apparatus depends on the treatment setting. The treatment setting may be inputted to the controller by an input device, such as a virtual button icon 38 on the touch sensitive display 20.

In other terms the various types of extracorporeal circuits differ mainly in the respective tube diameters and/or venous and arterial chamber volume or shape.

Figure 3:
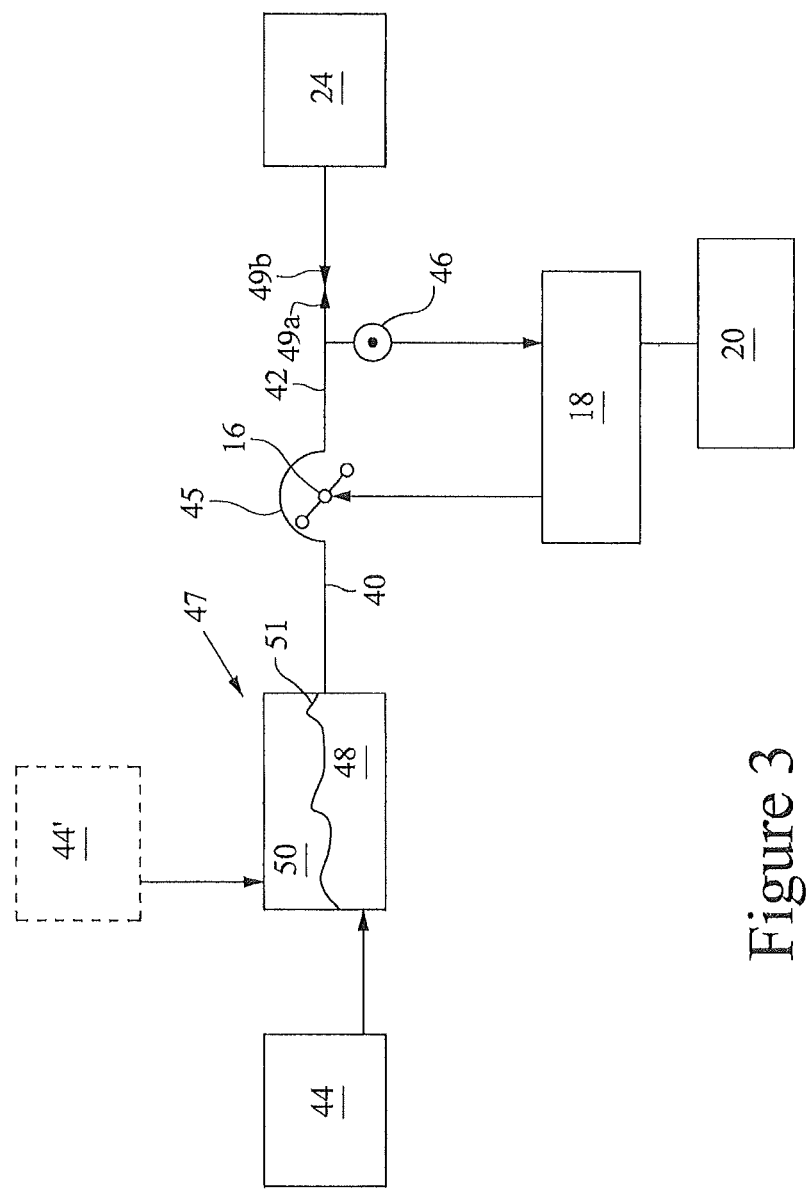
FIG. 3 is a schematic diagram of an extracorporeal blood treatment assembly with separable extracorporeal circuit.

FIG. 3 is a schematic diagram of an extracorporeal treatment assembly including the extracorporeal treatment apparatus 10 and extracorporeal circuit which is represented by tubing passages 40 and 42. The configuration of the treatment assembly and circuit shown in FIG. 3 is for priming the circuit with a priming liquid provided from a source of priming liquid 44 or 44'. The priming liquid may be a saline solution or other liquid, such as supplied by a liquid storage container 22 (FIG. 2) the priming liquid may alternatively be on-line prepared by the machine receiving water from a continuous water source. The priming liquid is pumped into the passages 40, 42 of the circuit during a pre-treatment operation performed by the treatment assembly. The priming liquid may purge the passages 40, 42 of air and other gases to insure that air or gases are not infused into the vascular system of a patient during the initiation of blood treatment.

The priming liquid may be pumped from a liquid source 44, 44' connected to a blood treatment device, such as a blood filter 47. The priming liquid source 44 may be connected to a blood chamber 48 of the filter 47 or the source 44' may be connected to a filtrate chamber 50 of the filter. A permeable membrane 51 separates the filtrate chamber from the blood chamber, and allows priming liquid to move between the blood and filtrate chambers. A pump 16 (FIG. 2) may receive a portion of the passage 42 such as a loop 45 of tube passage which may be mounted in the track of a peristaltic pump. The pump may move liquid through the passages 40, 42 by rollers which move against the loop of the tube passage and positively displace the liquid through the passage.

The pressure sensor 46 may be positioned to sense pressure in a portion of the passage 42 extending between the pump 16 and an outlet connector 49a, e.g., a female Luer connector. Luer connector assemblies, including a male and female connectors, are used to connect extracorporeal tube passages to other components such as catheters, containers which dispense or receive liquids, and implanted blood ports.

The pressure sensor 46 may also be mounted on the rigid frame 32, for example being active on one of the arterial and venous chamber to detect the fluid pressure in the chamber.

During the priming operation, the Luer connector 49a of the passage 42 may connect to a matching male Luer connector 49b at the inlet of the drainage container 24. The Luer connectors 49a, 49b when coupled tougher form a non-leaking and air tight connection between the passage 42 and the drainage container 24. The priming liquid draw from the source 44, 44', flows through the blood treatment device 47, the tubes 40, 42 and into the drainage container 24. The motive force for the priming liquid flow is the pump 16 acting on the tubes 40, 42. The priming operation is continued to ensure that the tubes 40, 42 are filled with liquid and purged of gases.

Figure 4:
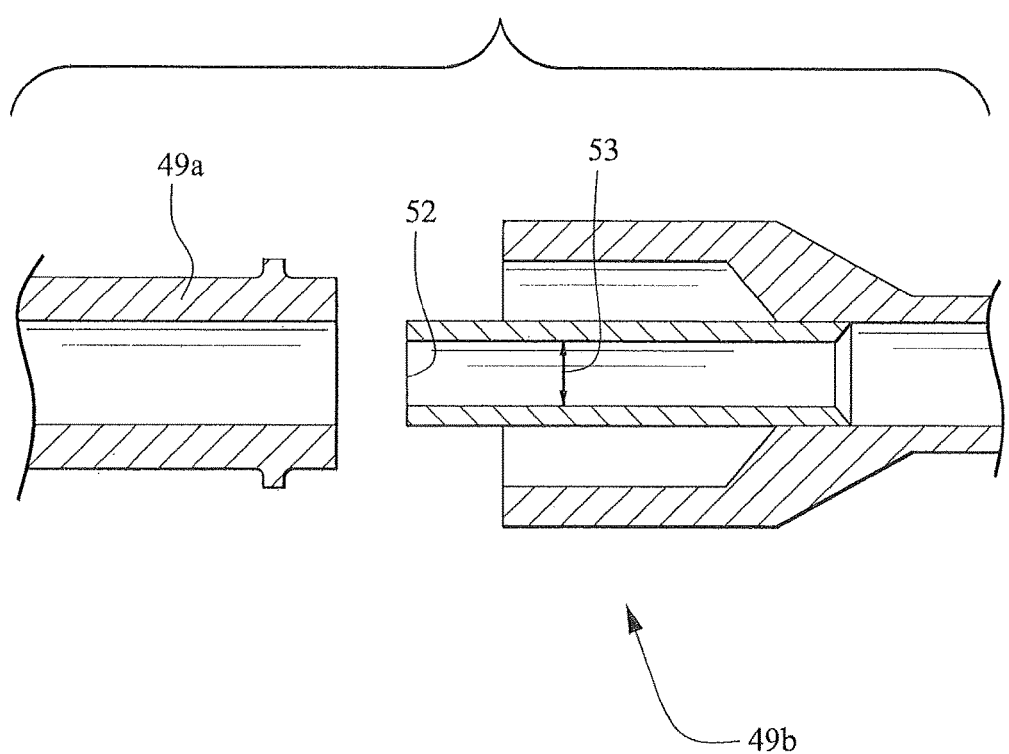
FIG. 4 is a flow diagram illustrating the flow impedance at an outlet of the extracorporeal circuit.

FIG. 4 illustrates the flow through the passage 42 and the impedance to the flow due to the male Luer connector 49b at the inlet of the drainage connector. The Luer connector 49b and inlet to the drainage container 24 have an impedance 52 to the flow of liquid. The impedance 52 may be a constant or a known flow resistance to the priming liquid being pumped into the drainage container. As shown in FIG. 4, the impedance 52 at the inlet to the male Luer connector 49b may be due to a narrow throat 53 of that connector. The impedance 52 at the Luer connector 49b may be substantial, such as representing at least fifty percent (50%) of the impendence to the flow of liquid through the passage 42 between the pump 16 and the drainage container 24.

The impedance 52, e.g. the flow resistance, at the inlet to the male Luer connector 49b remains uniform or constant regardless of the type of extracorporeal circuit connected to the treatment apparatus. The flow impedance 52 affects the upstream pressure in the passage 42 as the impedance applies a backpressure to the liquid flow through the passage. The pressure sensor 46 monitors the pressure in the passage 42. The pressure in the passage 42 as sensed by the pressure sensor 46 is, in part, a function of the impedance 52 at the inlet to the Luer connector 49b in the passage 42.

Figure 5:
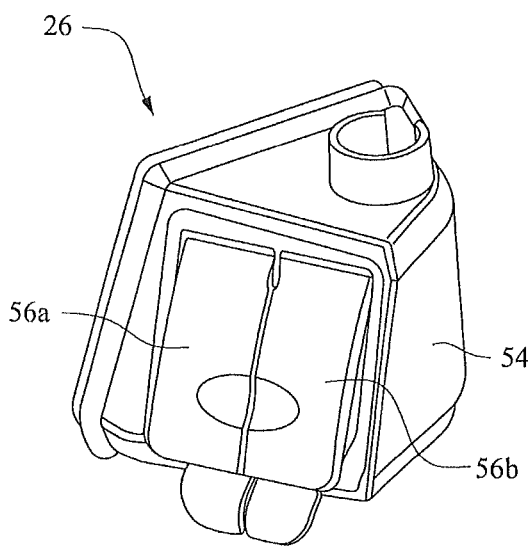
Figure 6:
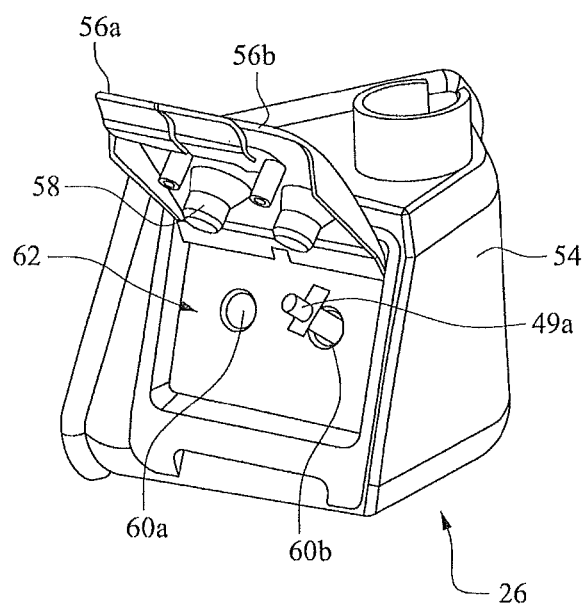

FIGS. 5 and 6 are perspective views of an exemplary housing 54 for the drainage inlet 26 for the liquid discharge container 24 (see FIG. 1). The housing may mount to the side of the extracorporeal treatment apparatus, as is shown in FIG. 1. The housing includes a cover door 56a, 56b. FIG. 5 shows the cover door 56a, 56b closed and FIG. 6 shows the door open. The inside surface of the door may include plugs 58 that fit into, when the door is closed, input ports 60a, 60b on the front face 62 of the housing. The input ports 60a, 60b may comprise male Luer connectors 49b which receives the female Luer connectors 49a of the passage 42 of the blood circuit. The doors 56a, 56b may a single door or a pair of doors such that one door may be opened to expose one of the ports 60a, 60b while the other door is closed to seal the other port 60a, 60b.

Figure 7:
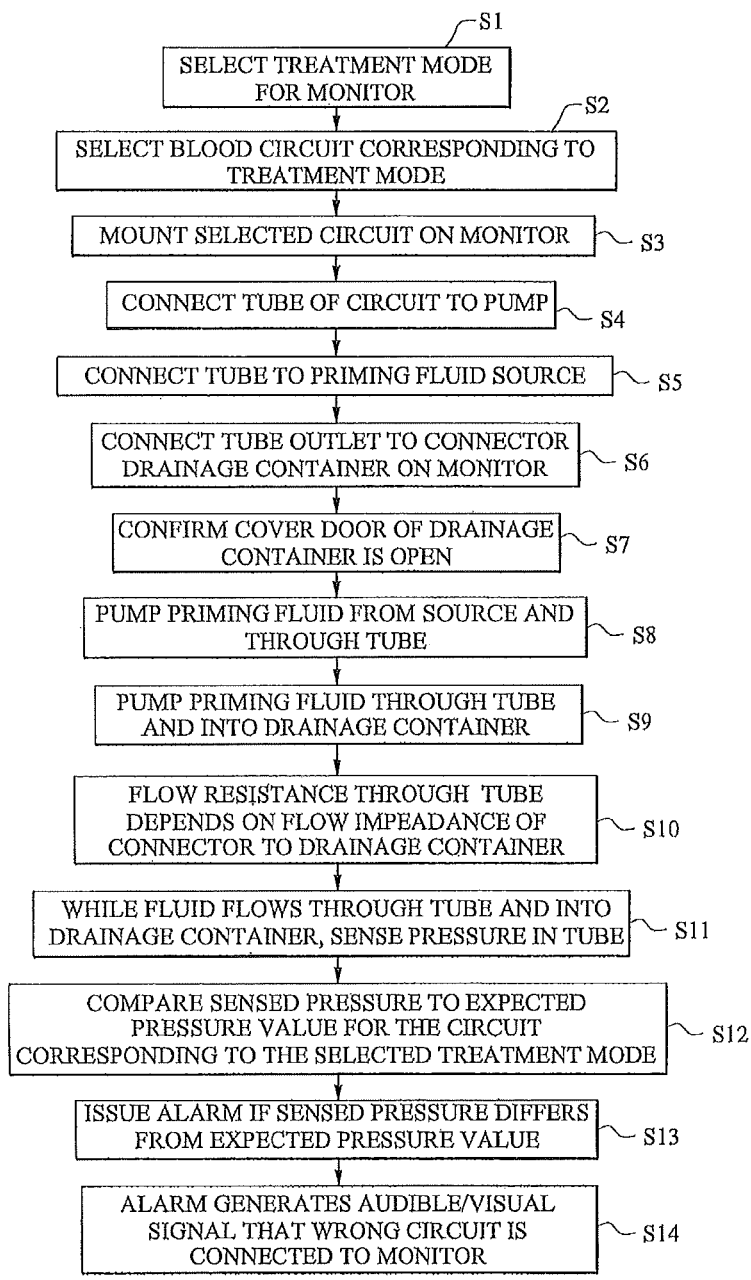
FIG. 7 shows a flow chart of an exemplary process for determining whether the proper extracorporeal circuit is connected to an extracorporeal treatment apparatus.

FIG. 7 is a process chart illustrating an example of a method for setting operational mode (conditions) of an extracorporeal treatment apparatus, and checking the type of extracorporeal circuit mounted to the apparatus. The process flow may involve a pressure check of the blood circuit conducted while a passage of the circuit is connected to a port connected to or otherwise associated with the treatment apparatus.

In one embodiment, the pressure check may be performed during a liquid priming process that occurs before the extracorporeal treatment procedure. The pressure check may be performed by the extracorporeal treatment apparatus to confirm or determine that the extracorporeal circuit connected to the apparatus is a type of circuit that corresponds to the operational settings of the apparatus. The pressure check is performed while a liquid passage of the circuit is connected to a coupling having a liquid flow impedance/resistance of a known or constant value. The pressure check involves monitoring the liquid pressure in a passage of the extracorporeal circuit while priming liquid flows through the passage and to a drainage container in the apparatus to collect the priming liquid.

A treatment mode is selected for the treatment apparatus, e.g., the monitor, in step S1. The treatment mode may be selected by the human operator interacting with the touch screen display to input a selected treatment mode command into the screen. The command is processed by the controller of the monitor to select from electronic memory settings, e.g., pump speeds, and desired pressure range(s), for the pressures to be sensed by the pressure sensor monitoring the passages in the circuit during treatment. The settings are selected from available settings for various treatments wherein the selected settings correspond to the settings matching the treatment mode inputted by the operator. These settings are stored in the memory of the controller. The settings may be specific to one or more of the possible extracorporeal circuits that may be connected to the monitor.

The operator selects an extracorporeal circuit in step S2 and mounts the selected circuit to the monitor in step S3. The mounting of the circuit to the monitor may include connecting one or more loops of the passages in the circuit to the pump, step S4, and connecting an end of one or more of the tubular passages in the circuit to the source of priming liquid, step S5.

The selected extracorporeal circuit should be the type of circuit appropriate for the operational settings that have been selected by the user for the desired treatment mode. There is a remote possibility that the operator inadvertently selects the wrong type of circuit and mounts the wrong circuit to the monitor. The pressure check provides an automatic technique to detect if the wrong type of extracorporeal circuit is connected to the monitor.

In step S6, the operator connects an outlet of a tubular passage, e.g., blood tube 42 (FIG. 3) to a liquid drainage container, such as container 24 shown in FIGS. 1 and 3. The outlet of the passage 42 may have a Luer connector 49a that fits in a matching Luer connector 49b in one of the inlet ports 60a, 60b of the inlet housing 26 for the drainage container 24. The monitor may check whether the doors 56a, 56b on the housing 54 is open before pumping priming liquid through the blood circuit in step S7. The door open check is a safeguard to avoid pumping priming liquid when the outlet end of the passage(s) in the circuit are not connected to a container to receive the priming liquid after flowing through the circuit. The monitor may not start pumping if one or more of the doors are closed, which the monitor believes should be opened.

The priming liquid is pumped through the circuit in step S8 by the monitor actuating the pump(s) to cause the priming liquid to flow from the source 44, 44' of priming liquid and through the passages of the circuit. The liquid may cause the priming liquid to be pumped through the passages in the extracorporeal circuit for a certain period in step 9, which is sufficiently long to ensure that the liquid is flowing through the entire passage(s) of the blood circuit. Alternatively or in addition to, the liquid may receive data indicating that the priming liquid is flowing into the drainage or drainage container, such as from a weight scale monitoring the weight of the drainage container.

As the priming liquid flows through the passage 42 and into the drainage container, the flow is resisted by constant or known flow impedance 52 at the connection between the passage and the inlet to the drainage container, in step S10. The flow impedance may be created by a Luer connector that couples the outlet of the blood passage to the drainage container.

For example, the male Luer connector 49b has a constant impedance 52, e.g., flow resistance, to liquid flow. The flow impedance of the Luer connector may be on the order of or greater than the flow impedance of the blood passage. The flow impedance of the Luer connector may be a significant contributor or the primary contributor to the total flow impedance to liquid flow through the blood passage from the pump to the drainage connector. The pump speed determines the rate at which liquid flows through the passage which influences the liquid pressure in the passage. The impedance of the blood passage also influences the pressure of the liquid flowing through the passage.

The liquid causes the pump to move the priming liquid through the passage(s) in the blood circuit at a flow rate that may be unique to the type of circuit corresponding to the operating settings for the treatment apparatus. As the priming liquid is pumped through the circuit passage, the pressure in the passage is measured by a pressure sensor 46 (FIG. 3), in step S11. The pressure may be measured repeatedly over a period, such as ten seconds, and an average pressure calculated. The average pressure may be compared to known pressure ranges stored in the controller. The pressure check is performed while liquid, e.g., a priming liquid, is continuously being pumped and flowing through a liquid passage in the extracorporeal blood circuit. The liquid pressure in the passage depends on the flow impedance, e.g., restriction, due to the Luer connector, the pump speed and size of the blood passage. The flow impedance due to the male Luer connector 49b, is constant and does not change with different types of extracorporeal circuits.

The pump speed depends on the treatment setting of the extracorporeal treatment apparatus. The pump speed specified in a particular treatment setting will generally create a pressure in the passage in a known pressure range. If the size, e.g., diameter, of the passage differs from the passage size of the type of circuit corresponding to the treatment setting, the pressure in the passage will be outside of the expected pressure range for the treatment. The size of the passage may differ from the expected size if the wrong circuit is connected to the apparatus. A pressure that does not fall within the prescribed pressure range for the expected extracorporeal circuit indicates that the wrong circuit is connected to the apparatus.

In step S12, the measured pressure obtained from the pressure sensor is compared by the controller to a prescribed range of acceptable pressures for the type of circuit that corresponds to the operational settings of the extracorporeal treatment apparatus. If the sensed pressure is outside the prescribed range, a determination may be made that the wrong circuit is connected to the extracorporeal treatment apparatus, in step S13. An alarm, sound and visual, may be issued by the controller if the determination is that the wrong circuit type is mounted to the monitor, in step S14.

The pressure check of the extracorporeal blood circuit may also include a determination of whether the circuit has a liquid leak in the liquid passage between the pump connection and the output of the passage. If the measured pressure in the liquid passage during pumping of the priming fluid or other fluid, such as blood during treatment, drops below a threshold pressure level, a determination may be made by the controller that the passage is leaking or that the coupling at the end of the passage leaks. Based on such a determination an alarm may be issued by the controller or the pumps may be stopped to cease liquid flow through the passages of the circuit.

In addition or as an alternative to determining whether the measured pressure in the passage 42 is within a prescribed range, the controller may adjust the pump speed to achieve a desired pressure in the flow through the passage in the blood circuit. The controller monitors the measured pressure in the passage and adjusts the pump speed to achieve the desired pressure. When the desired pressure is achieved, the pump speed is compared to a known range of acceptable pump speeds corresponding to the type of extracorporeal circuit expected to be connected to the extracorporeal treatment apparatus, given the operational settings for the apparatus. If the actual pump speed is outside of the range of acceptable pump speeds, the controller may issue an alarm or stop the pumps.

Further, the pressure check is performed to detect the type of extracorporeal circuit connected to the extracorporeal treatment apparatus. The controller may perform the pressure check on the extracorporeal treatment apparatus in one of the manners described above. The controller will interpret the results of the pressure check to determine which type of extracorporeal circuit is connected to the extracorporeal apparatus. For example, the controller compares the measured pressure of the priming liquid flowing through the passage to each of the expected pressure ranges corresponding to each of the extracorporeal circuits.

The controller may determine the type of the circuit that is connected to the apparatus based on which pressure range the measured pressure falls within. Once the determination is made of the type of circuit mounted to the apparatus, the controller may select and display the operational settings for the apparatus that correspond to the type of circuit determined to be mounted to the apparatus. The controller may also display the circuit type which is detected or present a list of possible circuits if the sensed flow pressure is within the pressure ranges for two or more circuits. The operator may view the display and confirm that the determination of the treatment mode, operation settings and type of blood circuit are correct before initiating blood treatment.

A further embodiment may be for the controller to monitor the power needed to drive the pump, e.g., current load, as an alternative or in addition to monitoring the pressure in the liquid passage in the extracorporeal circuit. The power needed to drive the pump is related to the pressure of the liquid being pumped. The greater the pressure the greater the power needed to drive the pump. Accordingly, the power driving the pump may be used as a substitute for or a check of the pressure sensor measuring the liquid pressure in the liquid passage.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. An extracorporeal treatment apparatus configured to receive an extracorporeal circuit, the treatment apparatus comprising:
 a pump configured to pump a liquid through a passage in the extracorporeal circuit while the circuit is mounted to the treatment apparatus;
 a flow coupling connectable to an outlet of the passage, wherein a flow impedance at the flow coupling is a constant or known value, and wherein the flow impedance at the flow coupling is due to a flow restriction having a smaller cross-sectional flow area for the liquid than any portion of the liquid passage extending from the pump to the flow coupling; and
 a controller which is configured to:
  store a flow resistance value at the flow coupling, said flow resistance value being either a value set by the operator before starting the apparatus or a pre-stored constant value known by the controller before starting the apparatus;
  control the pump at a speed corresponding to a set fluid flow value to move liquid through the passage and the flow coupling;
  collect actual data indicative of a pressure condition of the liquid flowing through the passage and flow coupling during control of the pump at said speed;
  store circuit type data uniquely corresponding to an expected circuit type mounted to the treatment apparatus out of a plurality extracorporeal circuit types that may be mounted to the treatment apparatus;
  retrieve a sectional dimension of the mounted circuit type based on said circuit type data uniquely corresponding to the mounted circuit type;
  determine expected data indicative of an expected pressure value of the liquid flowing through the passage and flow coupling as a function of the set fluid flow value or pump speed and of the sectional dimension of the mounted circuit type and as a function of said flow resistance value;
  compare the expected data with the actual data; and
  determine as a function of the comparing step whether the expected circuit type
 corresponds to the circuit type actually mounted on the apparatus.

2. The extracorporeal treatment apparatus of claim 1, wherein the controller is further configured to:
 determine an operational setting for the treatment apparatus or determine whether a current operational setting is proper based on the type of extracorporeal circuit corresponding to an identified parameter value.

3. The extracorporeal treatment apparatus of claim 1, wherein the actual data is data output by a pressure sensor monitoring the pressure of the liquid flowing through the passage.

4. The extracorporeal treatment apparatus of claim 1, further comprising a pressure sensor monitoring the pressure of the liquid flowing through the passage, a signal from the pressure sensor being received by the controller.

5. The extracorporeal treatment apparatus of claim 1, wherein the actual data indicative of the pressure is collected during a priming operation of the apparatus.

6. The extracorporeal treatment apparatus of claim 1, wherein the controller is configured to perform the steps of controlling, collecting, identifying and determining during a priming operation of the apparatus and/or before starting an extracorporeal blood treatment operation, at least the steps of controlling and collecting being performed during a priming operation of the apparatus and the steps of identifying and/or determining being performed either during a priming operation of the apparatus or after the priming operation and before starting the extracorporeal blood treatment operation.

7. The extracorporeal treatment apparatus of claim 5, wherein the actual data indicative of the pressure is received substantially at the end of the priming.

8. The extracorporeal treatment apparatus of claim 1, wherein the flow coupling includes an inlet coupling to a liquid drain.

9. The extracorporeal treatment apparatus of claim 1, wherein the flow coupling includes a protruding portion configured to connect to the outlet of the passage by direct insertion into the outlet of the passage, the protruding portion defining internally a flow conduit receiving the fluid and directing the fluid towards a liquid drain.

10. The extracorporeal treatment apparatus of claim 9, wherein the protruding portion is in the form of a substantially circular tube, said tube having a smooth outer lateral surface without means for attaching to the passage.

11. The extracorporeal treatment apparatus of claim 9, wherein the flow coupling includes an external crown at least partially embracing the protruding portion, the external crown including a structure for attaching to the passage.

12. The extracorporeal treatment apparatus of claim 1, wherein the flow coupling comprises a male Luer connector for coupling to a corresponding female Luer connector of the passage.

13. The extracorporeal treatment apparatus of claim 1, wherein the controller is configured to further automatically check that the passage is connected to the flow coupling prior to the actuation of the pump.

14. The extracorporeal treatment apparatus of claim 1, comprising a sensor configured to sense a specific condition of the flow coupling, said specific condition being either a non coupled condition of the flow coupling to the passage or a condition in which coupling between the flow coupling and the passage is possible.

15. The extracorporeal treatment apparatus of claim 14, wherein the specific condition sensed by the sensor is a condition of an open door allowing coupling of the flow coupling to the passage or of a closed door indicating a non coupled condition of the flow coupling to the passage.

16. The extracorporeal treatment apparatus of claim 1, wherein the confirmation that the liquid passage is connected to the drainage container includes determining if a door covering a liquid connection is open.

17. The extracorporeal treatment apparatus of claim 1, wherein the flow coupling includes a connector included in an inlet portion of a drainage container.

18. The extracorporeal treatment apparatus of claim 1, wherein the flow coupling includes a Luer connector.

19. The extracorporeal treatment apparatus of claim 1, wherein the controller is configured to sense the liquid pressure for a certain period of pumping, the sensed pressure determined based on several pressure sensing events during the certain period.

20. The extracorporeal treatment apparatus of claim 19, wherein the sensed pressure is an average of the pressures measured during the pressure sensing events.

21. The extracorporeal treatment apparatus of claim 1, wherein the extracorporeal circuit may be one of a plurality of selectable types of circuits and the liquid passage in at least one of the circuit types has a different size than the liquid passage in another one of the circuit types.

22. The extracorporeal treatment apparatus of claim 1, wherein the pump is an occlusive pump, and the passage is a deformable tube, wherein the pumping includes the pump pinching the tube to move the priming liquid through the passage.

23. The extracorporeal treatment apparatus of claim 1, wherein the flow impedance at the flow coupling is the flow resistance at the flow coupling.

24. The extracorporeal treatment apparatus of claim 1, wherein the controller has a memory storing a flow resistance value at the flow coupling, said flow resistance value being either a value set by the operator before starting the apparatus or a pre-stored constant value known by the controller before starting the apparatus.

25. The extracorporeal treatment apparatus of claim 1, wherein the controller is not configured to calculate a flow resistance of the flow coupling.

26. The extracorporeal treatment apparatus of claim 1, wherein the flow coupling determines a local loss of head in the extracorporeal circuit.

27. The extracorporeal treatment apparatus of claim 1, wherein said circuit type data uniquely corresponding to the mounted circuit type is acquired by the apparatus or set by the operator before starting an extracorporeal blood treatment operation.

28. The extracorporeal treatment apparatus of claim 1, wherein the plurality of extracorporeal circuit types differ in respective cross-sectional flow area of a respective passage, the flow coupling connectable to an outlet of each respective passage.

29. The extracorporeal treatment apparatus of claim 1, wherein the flow impedance at the flow coupling is greater than a flow impedance of the passage from the pump to the flow coupling.

30. An extracorporeal treatment apparatus configured to receive an extracorporeal circuit, the treatment apparatus comprising:
a pump configured to pump a liquid through a passage in the extracorporeal circuit while the circuit is mounted to the treatment apparatus;
a flow coupling connectable to an outlet of the passage, wherein a flow impedance at the flow coupling is a constant or known value, wherein the flow impedance at the flow coupling is due to a flow restriction having a smaller cross-sectional flow area for the liquid than any portion of the liquid passage extending from the pump to the flow coupling, and wherein the flow restriction is placed at the flow coupling; and
a controller which is configured to:

control the pump to move liquid through the passage and the flow coupling;

collect data indicative of a pressure condition of the liquid flowing through the passage and flow coupling;

identify a parameter value which correlates to the indicated pressure condition, wherein the identified parameter value is one of a plurality of known parameter values or ranges, wherein each value or range of values uniquely corresponds to a circuit type of a plurality extracorporeal circuit types that may be mounted to the treatment apparatus; and determine an operational setting for the treatment apparatus or determine whether a current operational setting is proper based on the type of extracorporeal circuit corresponding to the identified parameter value.

31. The extracorporeal treatment apparatus of claim 30, wherein the plurality of extracorporeal circuit types differ in respective cross-sectional flow area of a respective passage, the flow coupling connectable to an outlet of each respective passage.

32. An extracorporeal treatment assembly including a pump configured to pump a liquid through a passage in an actual extracorporeal circuit while the circuit is mounted to the treatment apparatus, a flow coupling connectable to an outlet of the passage wherein a flow impedance at the flow coupling is a certain flow impedance value, and a controller with a non-transitory storage storing instructions which when performed by the controller cause the assembly to:

control the pump to pump a liquid through the passage and the flow coupling at a rate corresponding to a certain fluid flow rate;

collect actual fluid pressure data indicative of a fluid pressure of the liquid flowing through the passage and flow coupling while the pump is pumping;

store circuit type data which uniquely corresponds to a certain type of extracorporeal circuit wherein data regarding a plurality of extracorporeal circuit types may be stored;

determine a dimension of the certain type of extracorporeal circuit based on the stored circuit type data;

determine an expected fluid pressure of liquid flowing through the passage and flow of the certain type of extracorporeal circuit, wherein the expected fluid pressure is determined using a set fluid flow rate or pump speed, the dimension of the certain type of extracorporeal circuit and the certain flow impedance value;

compare the actual fluid pressure data and the expected fluid pressure; and based on the comparison, determine whether the certain type of extracorporeal circuit corresponds to the actual extracorporeal circuit, wherein the flow impedance at the flow coupling is due to a flow restriction having a smaller cross-sectional flow area for the liquid than any portion of the liquid passage extending from the pump to the flow coupling.

33. The extracorporeal treatment apparatus of claim 32, wherein the plurality of extracorporeal circuit types differ in respective cross-sectional flow area of a respective passage, the flow coupling connectable to an outlet of each respective passage.

34. The extracorporeal treatment apparatus of claim 32, wherein the flow impedance at the flow coupling is greater than a flow impedance of the passage from the pump to the flow coupling.

* * * * *